(12) United States Patent
Mader

(10) Patent No.: US 6,620,907 B2
(45) Date of Patent: Sep. 16, 2003

(54) PROCESS FOR THE ELIMINATION OF MATERIALS CONTAINING HYDROLYZABLE HALIDES AND OTHER HIGH MOLECULAR WEIGHT MATERIALS FROM EPIHALOHYDRIN DERIVED EPOXY RESINS

(75) Inventor: Roger A. Mader, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 31 days.

(21) Appl. No.: 09/974,201

(22) Filed: Oct. 9, 2001

(65) Prior Publication Data

US 2002/0022709 A1 Feb. 21, 2002

Related U.S. Application Data

(63) Continuation-in-part of application No. 09/454,558, filed on Dec. 7, 1999, now abandoned.

(51) Int. Cl.$^7$ .............................. C08F 6/28; C08G 59/06
(52) U.S. Cl. ...................... 528/486; 525/527; 525/930; 528/488; 528/489; 528/492
(58) Field of Search .......................... 528/95, 488, 489, 528/486, 492; 523/457; 525/524, 527, 930; 549/542

(56) References Cited

U.S. PATENT DOCUMENTS

| | | | |
|---|---|---|---|
| 3,213,113 A | 10/1965 | Randall et al. ............. | 549/542 |
| 3,291,758 A | 12/1966 | Treaftis ................... | 523/459 X |
| 3,309,384 A | 3/1967 | Shimp et al. ............... | 528/95 |
| 3,417,050 A | 12/1968 | Price et al. | |
| 4,032,598 A | * 6/1977 | Fujiwara et al. ........ | 528/492 X |
| 4,395,542 A | 7/1983 | Sury ......................... | 528/481 |
| 4,447,598 A | 5/1984 | Caskey et al. .............. | 528/489 |
| 4,485,221 A | 11/1984 | Krueger et al. ............. | 525/507 |
| 4,535,150 A | 8/1985 | Hunter ....................... | 528/489 |
| 4,668,807 A | 5/1987 | Darbellay et al. .......... | 549/542 |
| 4,785,061 A | 11/1988 | Wang et al. ................ | 525/507 |
| 4,810,776 A | 3/1989 | Karlhuber et al. ......... | 528/488 |
| 4,829,104 A | 5/1989 | McIntyre et al. ........... | 523/403 |
| 4,895,755 A | 1/1990 | Berman et al. ............. | 428/290 |

FOREIGN PATENT DOCUMENTS

| | | | |
|---|---|---|---|
| DE | 203 056 | 10/1983 | |
| EP | 0 028 810 A2 | 5/1981 | |
| EP | 0 303 901 A2 | 2/1989 | |
| EP | 0 441 284 A2 | 8/1991 | |
| JP | 3-68568 | 3/1991 | ................. 549/542 |
| WO | WO 97/44335 | 11/1997 | |
| WO | WO 01/42230 A1 | 6/2001 | |

OTHER PUBLICATIONS

Kramkowski et al., "Extraction of pure diglycide bisphenol A ether through molecular distillation of crude Epidian–6", Institute of Chemical Engineering and Thermal Systems of the Wroclaw Technical University, Przen. Chem. 1997, 76(11), pp. 483–484.
Technical Bulletin, "EPON Resin 825", Shell Chemical Company, SC:235–88.825, Jan. 1992.
Shell Resins, "EPON Resin 828", Shell Chemical Company, SC:235–96.828, Oct. 1996.
UIC Inc., "Short Path Vacuum Distillation From Laboratory To Production", 1997.
Standard Test Method for Color Transparent Liquids (Gardner Color Scale), ASTM Designation: D 1544–80 (Reapproved 1989).
Shell Analytical Method, HC–427E–91, "Determination of epoxide content of EPON Resins by titration with perchloric acid," 1991.
Dow Liquid Epoxy Resins, Dow Chemical Company, pp. 1–41, Form No. 296–224–790X–P&M, 1990.

* cited by examiner

Primary Examiner—Richard D. Lovering
(74) Attorney, Agent, or Firm—Lisa M. Fagan

(57) ABSTRACT

The present invention provides a process for eliminating contaminants from epihalohydrin-derived epoxy resins. Another embodiment of the present invention is an epoxy product formed using said process. Yet another embodiment of the present invention is an epoxy derived in part from epihalohydrin wherein said epoxy is has a hydrolyzable halogen content of less than 10 ppm and an epoxide equivalent weight within 2 percent of the theoretical epoxide equivalent weight.

22 Claims, No Drawings

PROCESS FOR THE ELIMINATION OF MATERIALS CONTAINING HYDROLYZABLE HALIDES AND OTHER HIGH MOLECULAR WEIGHT MATERIALS FROM EPIHALOHYDRIN DERIVED EPOXY RESINS

CROSS-REFERENCE TO RELATED APPLICATION

This application is a Continuation-In-Part of patent application Ser. No. 09/454,558, filed Dec. 7, 1999, now abandoned.

FIELD OF INVENTION

This invention relates to a process for the elimination of undesirable materials from epihalohydrin-derived epoxy resins. More particularly, this invention relates to a process for eliminating materials containing hydrolyzable halides and other high molecular weight materials including those containing hydroxyl functionality from epihalohydrin derived epoxy resins.

BACKGROUND

Epihalohydrins are often used as an ingredient to prepare epoxy resins. Particularly useful in the preparation of epoxy resins is epichlorohydrin. For example, a dihydric phenol (or other active-hydrogen containing material) is often reacted with epichlorohydrin in the presence of a catalyst. The resulting products include the desired epoxy, high molecular weight materials including oligomers, residual epichlorohydrin, and other contaminants containing hydrolyzable chloride, etc. The preparation of pure epoxies is desirable. High molecular weight materials, such as, for example, oligomers or materials containing hydroxyl functionality, may interfere with the epoxy's performance.

One use for epihalohydrin-derived epoxies is in the electronics area. Some electronic applications where these epoxies are used include, but are not limited to, conformal coatings, high pressure laminations, castings, die attach adhesives, electrical pottings, encapsulations, and underfills. Hydrolyzable halide is a source of free halide in the presence of moisture. Thus, corrosion caused by a halide is a critical issue in the manufacture of electronic devices. Therefore, elimination of hydrolyzable halides is desirable.

Several methods or processes are known for purifying or isolating epoxies. One of these methods is using one or more separation processes such as stripping or distillation. Another method is reacting an alkali metal hydroxide solution or other solvent-based system and water-washing to remove the free chloride or phenolic salts.

Additionally, various methods or processes are known that reduce the amount of hydrolyzable halide in the epoxy product. For example, many methods have been described for the preparation of resins with low levels of hydrolyzable chloride. (See for example, U.S. Pat. No. 4,485,221). However, most of these methods involve extraction with an aqueous base and require organic solvents, which add expense and decrease process efficiency.

Therefore, the need exists for a process of eliminating hydrolyzable halides and other high molecular weight materials from epihalohydrin-derived epoxies that is safe, environmentally-friendly, versatile, efficient, and solventless.

SUMMARY OF INVENTION

The present invention provides a process for eliminating hydrolyzable halides and high molecular weight materials from epihalohydrin-derived epoxies. This process can be conducted by the epoxy manufacturer, or can be conducted on a commercially sold epoxy to reduce the level of or to eliminate hydrolyzable halide and high molecular weight materials present. The present invention comprises a process for eliminating hydrolyzable halides and high molecular weight materials from epihalohydrin-derived epoxy resins comprising the steps of: a) reacting an epoxy resin comprising materials containing hydrolyzable halides with a base wherein said base is present in a quantity that exceeds the molar equivalent based on the materials containing hydrolyzable halide; b) heating the mixture while agitating; c) neutralizing said heated mixture with carbon dioxide to form a crude product; and d) distilling said crude product using molecular distillation to yield a product.

Another embodiment of the present invention is a process for eliminating hydrolyzable halides and high molecular weight materials from epihalohydrin-derived epoxy resins comprising the steps of: a) distilling an epoxy resin comprising materials containing hydrolyzable halide using molecular distillation to yield an epoxy distillate; and b) reacting said epoxy distillate with a base wherein said base is present in a quantity that exceeds the molar equivalent based on the materials containing hydrolyzable halide.

Another embodiment of the present invention is an epoxy product formed using said contaminant elimination process. The epoxy product formed advantageously has low hydrolyzable halide content. Additionally, the epoxy product can have an epoxide equivalent weight at or near the theoretical value.

Yet another embodiment of the present invention is an epoxy derived from epihalohydrin that has low hydrolyzable halide content and that does not contain high molecular weight material.

The process of the present invention is solvent-free, relatively inexpensive, versatile, and environmentally-friendly. Moreover, the process of the present invention can be carried out using standard manufacturing equipment and in high volume.

The process of the present invention can be done in batch or as a continuous process.

DETAILED DESCRIPTION OF ILLUSTRATIVE EMBODIMENTS

The present invention provides a process for eliminating undesirable materials from epoxy resins that are derived from epihalohydrin. These undesirable materials or by-products are defined herein as including materials comprising hydrolyzable halides (such as, for example, hydrolyzable chloride, hydrolyzable bromide, or hydrolyzable iodide) and in some epoxy resins high molecular weight materials. Hydrolyzable halides are halide releasing materials. High molecular weight materials are defined herein as dimers and other materials having a molecular weight greater than the dimer. These high molecular weight materials can be oligomers that can contain hydroxyl groups. Other high molecular weight materials include, but are not limited to, reaction by-products, polymerized epoxies, phenolic salts, etc., and mixtures thereof. Examples of some high molecular weight materials that may be eliminated from some epoxy resins include, but are not limited to:

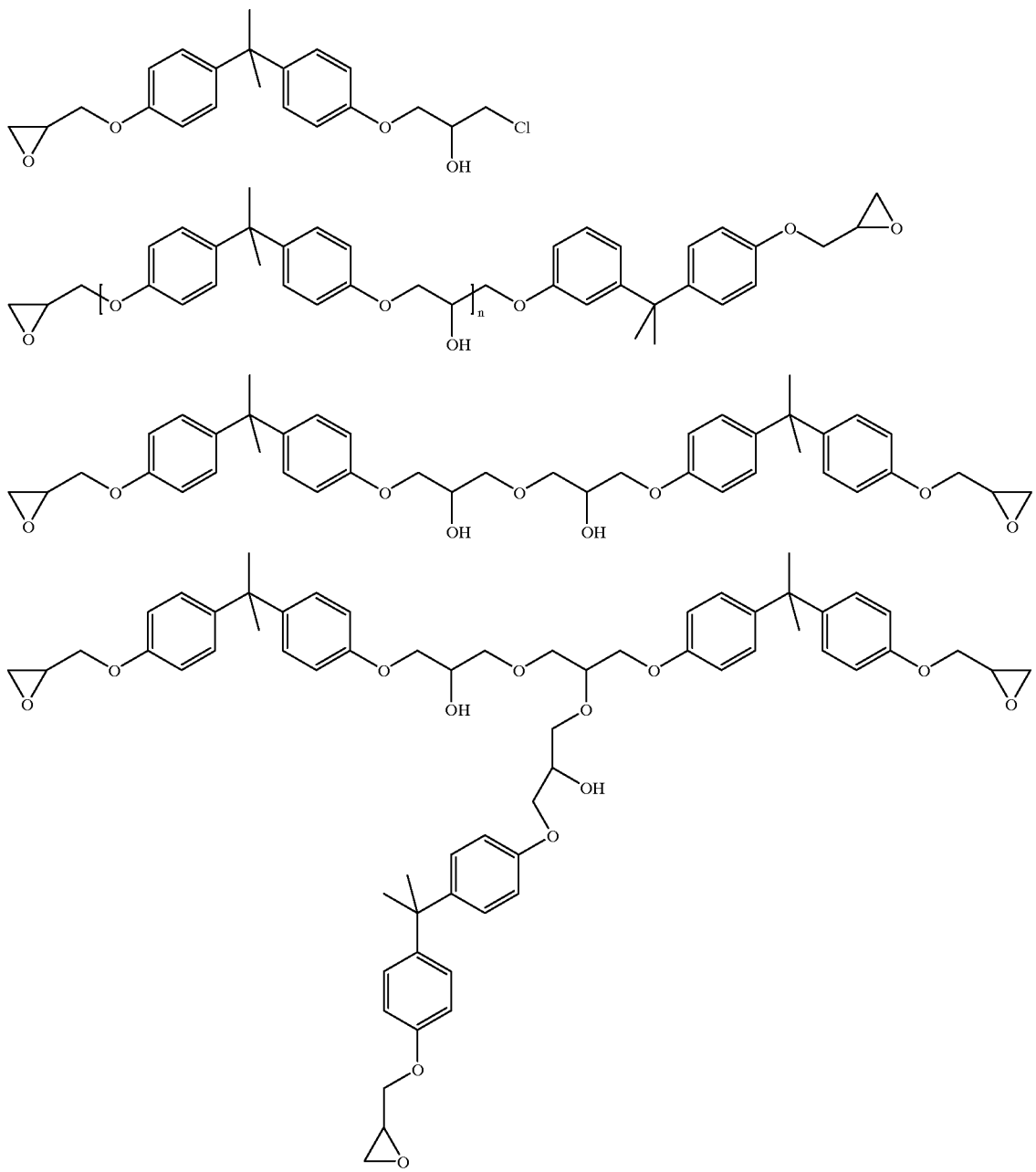

The process of the present invention has many advantages. For example, this process is a relatively inexpensive procedure for preparing epoxy resins that contain low levels (i.e., preferably 0.1 ppm to 100 ppm, more preferably less than 10 ppm, and most preferably less than 1 ppm) of hydrolyzable halide.

The epoxies of the present invention have an epoxide equivalent weight at or near the theoretical value expected for the specific monomer. Prior to the present invention, low molecular weight halide epoxies such as EPON™ Resin 828 (and its high purity version EPON™ Resin 825), available from Shell Chemical Company, Houston, Tex., is disclosed as having an epoxide equivalent weight of 185–192 (175–180 for EPON™ Resin 825) whereas the theoretical epoxide equivalent weight is 170. (See Shell Resins, SC:235-96.828, October 1996 and Technical Bulletin, Shell Chemical Company SC:235-88.825 January 1992). Whereas, using the present invention, starting with EPON™ Resin 828, an epoxide equivalent weight of 170 is obtained. The method used to obtain the epoxide equivalent weight is set forth in Example 1.

Additionally, the process is non-extractive and thus can be and is solventless. The process is run at 100 percent solids with only a small amount of base being added. Thus, the process is more environmentally-friendly than processes requiring solvents. There are no residual solvents in the epoxy product and therefore no outgassing. Further, this process is a non-solvent and chemical reagent waste generating process. If the high molecular weight materials that are eliminated are used, then the process of the present invention can be non-waste generating.

The process of the present invention is versatile. To purify different epoxy resins, one only needs to change the base in light of the starting epoxy resin. Therefore, the equipment, etc., can remain the same that helps to reduce cost. Further, the required equipment is readily available in the chemical industry.

The process advantageously eliminates oligomers and other high molecular weight materials including those high molecular weight materials containing hydroxyl groups that may not be desirable. Side reactions caused by contaminants are substantially or all-together eliminated. This may improve optical clarity and lower the molecular weight that affects the Theological properties of the epoxy and the resultant glass transition temperature of the cured epoxy. Depending on the curative employed, this elimination of by-products containing hydroxyl groups may provide enhanced pot life for the epoxy resin, which is advantageous in many applications.

Epoxy-resin

The epoxy resin that is purified using the present invention includes any epoxy resin that is derived from epihalohydrin or that contains hydrolyzable halides. Further, this epoxy resin must be distillable using molecular distillation. Therefore, the epoxy resin must not decompose during the distillation process.

The epoxy resins suitable for the present invention can contain materials containing hydrolyzable halides. For example, epoxy resins having hydrolyzable halide contents of 10,000 ppm and epoxy resins having hydrolyzable halide contents of 150 ppm are suitable for the process of the present invention. Further, the epoxy resins of the present invention may include other high molecular weight materials that can contain hydroxyl groups.

One example of an epoxy resin suitable for the process of the present invention can be prepared as illustrated below.

ethers, aliphatic diglycidyl ethers, aliphatic multifunctional glycidyl ethers, and aliphatic glycidyl esters.

Examples of useful bisphenol A-epichlorohydrin epoxy resins include, but are not limited to, EPON™ Resins 825, 826 and 828, available from Shell Chemical Company, Houston Tex., D.E.R.™ 330, 331, and 332, available from Dow Chemical Company, Midland, Mich., and ARALDITE™ GY 6008, GY 6010, and GY 2600, available from Ciba Specialty Chemicals, Brewster, N.Y.

Examples of useful bisphenol F-epichlorohydrin epoxy resins include, but are not limited to, EPON™ Resin 862, available from Shell Chemical Company, Houston, Tex., and ARALDITE™ GY 281, GY 282, GY 285, PY 306, and PY 307, available from Ciba Specialty Chemicals, Brewster, N.Y.

Examples of useful mono, di and multifunctional glycidyl ether resins include, but are not limited to, HELOXY™ Modifier 107 and HELOXY™ Modifier 48, available from Ciba Specialty Chemicals, Brewster, N.Y., and EPON™ 1510, available from Shell Chemical Company, Houston Tex.

Materials having groups that are sensitive to hydrolysis by strong bases such as epoxies having ester linkage are also suitable for the process of the present invention. For example, CY™ 184, available from Ciba Specialty Chemicals, Brewster, N.Y., is suitable for the process of the present invention.

Base Treatment

The process of the present invention comprises the step of treatment of or the reaction of the epoxy resin with a base. The base is present in an amount that exceeds the molar equivalent based on the materials comprising hydrolyzable halide. This amount depends on the starting epoxy resin. For example, if no other acids are present, a theoretical amount of base can be used based on the ppm of hydrolyzable halide. In other situations, for example, 100 percent to 200 percent base is required.

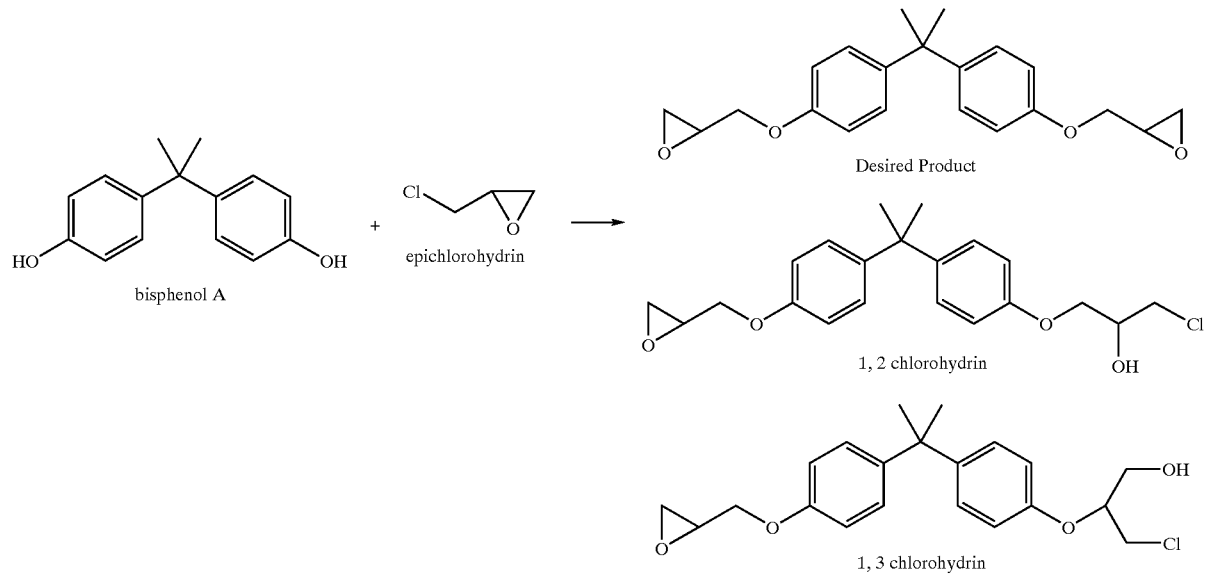

This epoxy resin contains the desired bisphenol A epoxy product, as well as 1,2 chlorohydrin (containing hydrolyzable chloride), and 1,3 chlorohydrin.

Examples of epoxy resins useful in the process of the present invention include, but are not limited to, bisphenol A-epichlorohydrin epoxy resins, bisphenol F-epichlorohydrin epoxy resins, aliphatic mono glycidyl The epoxy resin may be combined with a base at room temperature to form a mixture or in other situations, the epoxy resin may be pre-heated. Thus, the heating and agitation step may occur prior to and during the reaction with the base, simultaneously with the base treatment step, or after the base is added to the epoxy resin. This order is dictated by the starting epoxy resin.

The selection of the base depends upon the starting epoxy resin. Examples of suitable bases useful in the process of the present invention include, but are not limited to, hydroxides such as potassium hydroxide in water, sodium hydroxide, and lithium hydroxide, hydrides such as lithium hydride, sodium hydride (optionally in mineral oil), and potassium hydride, alkoxides such as primary, secondary, and tertiary (e.g., potassium t-butoxide in THF) alkoxides such as sodium ethoxide, carbonates such as potassium carbonate and sodium carbonate, and quaternary ammonium salts.

Generally, the base strength and the temperature are such that the halohydrin closes to the epoxy and under which the epoxy does not polymerize. For example, in one case for an epichlorohydrin-derived epoxy resin, potassium t-butoxide in THF was suitable at 25° C., but the resin polymerized at 70° C.

The use of non-nucleophilic bases such as sodium hydride are believed to have the advantageous effect of closing the halohydrin without reacting appreciably with other base (hydrolytically) sensitive functionality such as esters. Without being bound by theory, the following is believed to occur:

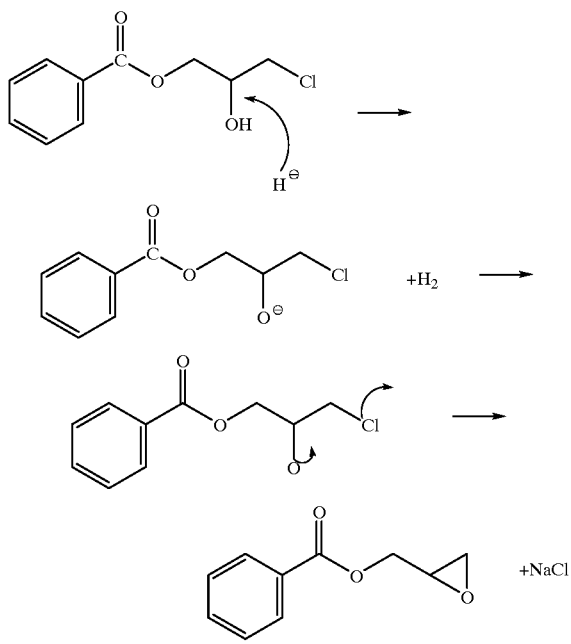

If a non-nucleophilic base is used, the process of the present invention preferably comprises the following steps: (a) distilling an epoxy resin comprising materials containing hydrolyzable halide using molecular distillation to yield an epoxy distillate; and (b) reacting said epoxy distillate with a base wherein said base is present in a quantity that exceeds the molar equivalent based on the materials containing hydrolyzable halide.

The initial distillation step removes moisture along with high molecular weight materials containing hydroxyl functionality. The product can either be neutralized with water and carbon dioxide to remove residual sodium hydroxide before distillation or can be distilled directly without neutralization.

Heating the Mixture while Agitating

The mixture is heated to a temperature suitable for reaction of the halohydrin to form the epoxy while agitated. For example, the mixture may be heated using a heat mantel. Generally, the mixture is heated between 20° C. to 200° C. for 1 minute to 12 hours. However, the temperature and time depend upon the starting epoxy resin, base strength and solubility, the catalytic activity of the base towards epoxy polymerization, and commercial viability.

This heating and mixing can occur after the epoxy resin and base are combined, prior to and during the base treatment step, or simultaneously with the addition of the base and base treatment step.

The mixture is usually heated to alter the viscosity, which in turn helps the dispersion of the base.

Neutralization of the Mixture

The heated mixture is then neutralized, if required, using carbon dioxide to form a crude product. With the hydrides, this neutralization step may not be required. Optionally, at this point, residual salts may be removed from the crude product by filtration.

Distillation

Next, the crude product is isolated by molecular distillation to yield the product. For example, a rolled film evaporator or wipe film evaporator may be used. With a rolled film evaporator, the crude product is distributed across a vertical heated surface by an efficient, self-cleaning roller wiper system into a uniform thin film. The evaporated material travels a short distance to an internal condenser. A lower vacuum pressure is used with low operating temperatures. (See UIC Inc., "Short Path Vacuum Distillation from Laboratory to Production", 1997). With a wipe film evaporator, a wiper is used instead of the self-cleaning roller wiper.

The distillation conditions depend on the boiling point of the crude product.

Noncondensible materials that may be in the starting materials, i.e., the epoxy resin, are removed during molecular distillation.

Product

The yielded epoxy product has low levels of hydrolyzable halide, i.e., preferably from 0.1 to 100 ppm, more preferably less than 10 ppm, and most preferably less than 1 ppm.

The yielded product is preferably free of high molecular weight materials. High molecular weight material-free is defined herein as having no dimers and materials having higher molecular weight than the dimer. The epoxide equivalent weight is at or near the theoretical epoxide equivalent weight (i.e., within 2 percent, preferably within 1 percent of the theoretical epoxide equivalent weight).

The epoxy product of the present invention has a higher cured glass transition temperature than the less pure version, which is advantageous. The epoxy product of the present invention is also more predictable due to product consistency. The viscosity is lower than the less pure version of the same epoxy resin. There is no residual base in the epoxy product, which is advantageous. Residual base may inhibit cationically cured epoxies. Other low hydrolyzable halide epoxy resins such as EPON™ Resin 1462, available from Shell Chemical Company, which have some residual base are described as having a yellow color (a Gardner Color Scale value of less than 3). The epoxy product of the present invention is colorless. For example, using the Gardner test (ASTM D1544-80), the Gardner Color Scale value is less than 0.1 for purified EPON™ Resin 828.

The process of the present invention can be batch or continuous.

Application

The epoxy products of the present invention are suitable in optical applications where clarity is an important property. As indicated above, a low Gardner Color value is obtainable.

The epoxy products of the present invention are suitable as a primer for other epoxy materials for aircraft and automotive applications where corrosion resistance may be important. Additionally, these epoxy products may be particularly useful as either a primer or adhesive on other metallic surfaces where corrosion is an issue.

The epoxy products of the present invention are also particularly suitable for high temperature applications where a high glass transition temperature is desirable.

EXAMPLES

The present invention will be further described with reference to the following nonlimiting examples and test methods. All parts, percentages, and ratios are by weight unless otherwise specified.

Example 1

In a 1 liter three-neck round bottom flask, equipped with a mechanical stirrer, nitrogen inlet, and temperature probe, was added 500 grams of EPON™ Resin 828 (689 ppm hydrolyzable chloride), available from Shell Chemical Company, Houston, Texas. This mixture was heated to about 70° C. and a premix of 1.5 grams of 85 percent potassium hydroxide in 1.5 grams of water was added. The resulting mixture was heated for about 4 hours and then dry ice was added and the mixing continued for about 30 minutes. This mixture was then cooled to room temperature. This gave a crude product which was distilled on a rolled film evaporator (model number KDL4, available from UIC Inc., Joliet, Ill.) at about 185° C. at about 0.001 mm vacuum to give 224 grams of clear colorless material.

The test method used to determine the hydrolyzable chloride content in epoxy resins utilizes ion chromatography and is based on ASTM D 1726-90. The test procedure was as follows: A boiled-out (18 Mohm water), empty 250 mL iodine flask was electronically tared. The epoxy sample (6–8 grams) was added to the flask, and the weight was recorded to the nearest 0.0001 gram. Blanks were carried, but with no sample added. 50 mL of THF and 10 mL of 0.1 N KOH/MeOH were added to the flask, and the mixture was heated at reflux for about 30 minutes and cooled to room temperature. 20 mL ultrapure water was added next along with 2.00 mL of NaCl solution (0.005 N) by means of a pipette. The solvents were then evaporated by gently heating via steamplate at about 80° C. under a nitrogen stream. The remaining aqueous solution was brought to a 100 gram total mass with ultrapure water and the weight recorded to the nearest 0.0001 gram. The solution was filtered using a syringe-tip BIO-RAD™, BIO-REX™ Strong Cation Exchange Membrane filter in $H^+$ form (catalog #343-0019, available from Bio-Rad Laboratories, Richmond, Calif.) (properly rinsed with methanol then water). The aqueous filtrate was analyzed by ion chromatography. The anion analysis was carried out using a Dionex DX500 Ion Chromatography System (available from Dionex Corporation, Sunnyvale, Calif.) (consisting of the DX500 quaternary gradient pump, AS3500 Autosampler, SRS Self-Regenerating Chemical Suppressor, and ED40 Electrochemical Detector with conductivity cell). A Dionex IonPac AS14 anion exchange column (IonPac AG14 guard column) and 3.5 mM sodium carbonate/1.0 mM sodium bicarbonate eluant were used to perform the separation. The mobile phase was delivered at a flow rate of 1.5 mL/min. The analysis used 50 µL injections for sample and standard solutions. The standards ranged from 0.1–25 ppm. The hydrolyzable chloride content was back-calculated based on the observed chloride content in each 50 µL sample solution, the initial sample size, and dilution volume.

Analysis showed that the hydrolyzable chloride was reduced to 2.2 ppm.

The test procedure for determining epoxide equivalent weight uses a stable titrant, perchloric acid which generates hydrobromic acid in situ by its action on either tetrabutylammonium bromide or tetrabutylammonium iodide. In this procedure, a weighed sample of 0.5–0.9 meq epoxy in 50 ml chloroform is dissolved. 10 ml of 10 percent tetrabutylammonium bromide (or tetrabutylammonium iodide) is added and then 10–20 ml of acetic acid is added. The sample is then titrated with 0.1 N $HClO_4$ to the potentiometric endpoint.

Using this method, the epoxide equivalent weight was 170 (theoretical value is 170).

Example 2

A sample of EPON™ Resin 862 (available from Shell Chemical Company) was distilled on a rolled film evaporator (model number KDL4) at about 170° C. and about 0.001 mm vacuum. 354 grams of distillate and 178 grams of residue were obtained. The distillate was kept under a nitrogen atmosphere and transferred to a flask equipped with a mechanical stirrer, nitrogen inlet, and temperature probe. 0.56 grams of 60 percent sodium hydride in mineral oil was added to the flask and the mixture was heated to about 80° C. at which point there was a slow evolution of hydrogen gas. The temperature was increased to about 100° C. and the mixture was held at that temperature until no more gas evolution was detected (about two hours). The reaction mixture was cooled to about 70° C. and dry ice added followed by 0.4 milliliters of water. More dry ice was added and the mixture cooled to room temperature. The crude product was distilled on a rolled film evaporator at about 170° C. and about 0.001 mm vacuum to give 214 grams of clear product. The level of hydrolyzable chloride was reduced from 126 ppm to <0.5 ppm as analyzed using the method disclosed in Example 1. Using the analysis method of Example 1, the epoxide equivalent weight was 157.8 (theoretical value is 157).

Example 3

To 252 grams of distilled EPON™ Resin 828 (available from Shell Chemical Company) was added 15 milliliters of 1 M potassium t-butoxide in THF. The mixture was heated to about 30° C. and stirred at that temperature for about 4 hours. After the addition of dry ice, the crude product was distilled on a rolled film evaporator (model number KDL4) at about 190° C. and about 0.001 mm vacuum to give 157 grams of clear product. The concentration of hydrolyzable chloride was <1 ppm using the analysis method disclosed in Example 1. Using the analysis method of Example 1, the epoxide equivalent weight was 173 (theoretical value is 170).

Example 4

A freshly distilled sample of Heloxy Modifier 107 (337 grams) was treated with 0.53 grams of 60 percent sodium hydride in mineral oil and heated to about 80° C. for about 7 hours. Work-up with dry ice and water as described in the previous examples gave a crude product which was distilled on a rolled film evaporator (model number KDL4) at about 155° C. and about 0.001 mm vacuum to give 278 grams of water white product. The amount of hydrolyzable chloride was reduced from 870 ppm to 43 ppm as analyzed using the analysis method disclosed in Example 1.

Example 5

To 233 grams of distilled EPON™ Resin 1510 (available from Shell Chemical Company) was added a premix of 0.67 grams of potassium hydroxide in 0.67 grams of water. The mixture was heated to about 70° C. for about 4 hours. The mixture was neutralized with dry ice and distilled on a rolled film evaporator (model number KDL4) at about 185° C. and about 0.001 mm vacuum to give 178 grams of colorless liquid. The amount of hydrolyzable chloride was reduced from 917 ppm to 32 ppm as analyzed using the analysis method disclosed in Example 1.

Example 6

In a 1 liter three-neck round bottom flask, equipped with a mechanical stirrer, nitrogen inlet, and temperature probe, was added 650 grams of D.E.R. 313M (407 ppm hydrolyzable chloride) available from Dow Chemical Company, Midland, Mich. This mixture was heated to about 70° C. and a premix of 4.0 grams of 50 percent aqueous potassium hydroxide was added. The resulting mixture was heated for about 4 hours and then dry ice was added and the mixing continued for about 30 minutes. This mixture was then cooled to room temperature. This gave a crude product which was distilled on a rolled film evaporator (model number KDL4) at about 185° C. at about 0.001 mm vacuum to give 433 grams of clear colorless material. Analysis showed that the hydrolyzable chloride was reduced to 13.9 ppm using the analysis method disclosed in Example 1. Using the analysis method of Example 1, the epoxide equivalent weight was 166.7 (theoretical value is 170).

Example 7

In a 500 milliliter, three neck round bottom flask which as equipped with a nitrogen inlet, a mechanical stirrer, and a temperature probe was added 354 grams of Araldite CY 184™ which had been previously distilled on a rolled film evaporator. This was heated to about 80° C. and to it was added 1.0 grams of 60 percent sodium hydride in mineral oil. The mixture was heated for 4 hours after which dry ice and water were added to quench the reaction. The mixture was cooled to room temperature and filtered on a Buchner funnel to remove salts. The filtrate was distilled on a rolled film evaporator at about 130° C. and about 0.02 mm Hg vacuum to give 248 grams. The amount of hydrolyzable chloride was reduced from 5071 ppm to 670 ppm using the analysis method of Example 1. Using the analysis method of Example 1, the epoxide equivalent weight was 141 (theoretical value is 142).

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims as set forth herein as follows.

What is claimed is:

1. A process for eliminating materials from epoxy resins comprising the steps of:
   a) reacting an epoxy resin comprising materials containing hydrolyzable halide with a base wherein said base is present in a quantity that exceeds a molar equivalent based on the materials containing hydrolyzable halide to form a mixture;
   b) heating said mixture while agitating;
   c) neutralizing said heated mixture with carbon dioxide to form a crude product; and
   d) distilling said crude product using molecular distillation to yield an epoxy distillate product.

2. The process according to claim 1, wherein said hydrolyzable halide is selected from the group consisting of chloride, iodide, and bromide.

3. The process according to claim 1, wherein said epoxy resin further comprises one or more high molecular weight material(s).

4. The process according to claim 3, wherein said high molecular weight material is selected from the group consisting of oligomers, polymerized epoxies, phenolic salts, reaction by-products, and mixtures thereof.

5. The process according to claim 1, wherein said epoxy resin is selected from the group consisting of bisphenol A-epichlorohydrin epoxy resins, bisphenol F-epichlorohydrin epoxy resins, aliphatic mono glycidyl ethers, aliphatic diglycidyl ethers, aliphatic multifunctional glycidyl ethers, and aliphatic glycidyl esters.

6. The process according to claim 1, wherein said epoxy resin has a hydrolyzable halide content ranging from 150 ppm to 10,000 ppm.

7. The process according to claim 1, wherein said base is selected from the group consisting of hydroxides, hydrides, alkoxides, carbonates, and quaternary ammonium salts.

8. The process according to claim 1, wherein in step (b) said mixture is heated to a temperature that allows said reaction to occur at a reasonable rate, but not that results in polymerization of said epoxy resin.

9. The process according to claim 1, wherein said molecular distillation uses a rolled film evaporator or a wipe film evaporator.

10. The process according to claim 1, wherein said product has a hydrolyzable halide content ranging from about 0.1 to about 100 ppm and an epoxide equivalent weight within 2 percent of the theoretical epoxide equivalent weight.

11. The process according to claim 1, wherein said product has an epoxide equivalent weight within 2 percent of the theoretical epoxide equivalent weight.

12. The process according to claim 1, wherein step (b) occurs prior to and during step (a).

13. The process according to claim 1, wherein step (b) occurs at the same time as step (a).

14. The process according to claim 1, wherein said process is batch or continuous.

15. An epoxy distillate product prepared using a process comprising the following steps:
   a) reacting an epoxy resin comprising a material containing hydrolyzable halide with a base wherein said base is present in a quantity that exceeds a molar equivalent based on the material containing hydrolyzable halide to form a mixture;
   b) heating said mixture while agitating;
   c) neutralizing said heated mixture with carbon dioxide to form a crude product; and
   d) distilling said crude product using molecular distillation to yield said epoxy distillate product.

16. The product according to claim 15, wherein step (b) occurs prior to and during step (a).

17. The product according to claim 15, wherein step (b) occurs at the same time as step (a).

18. An epoxy adhesive or primer derived in part from epihalohydrin wherein:
   a) said epoxy has a hydrolyzable halide content up to 10 ppm; and
   b) said epoxy has an epoxide equivalent weight within 2 percent of the theoretical epoxide equivalent weight.

19. An epoxy adhesive or primer derived in part from epihalohydrin wherein said epoxy has a hydrolyzable halide content ranging from 10 to 100 ppm and an epoxide equivalent weight within 2 percent of the theoretical epoxide equivalent weight.

20. A process for eliminating hydrolyzable halides and high molecular weight materials from epihalohydrin-derived epoxy resins comprising the steps of:
   a) distilling an epoxy resin comprising materials containing hydrolyzable halide using molecular distillation to yield an epoxy distillate; and
   b) reacting said epoxy distillate with a base wherein said base is present in a quantity that exceeds the molar equivalent based on the materials containing hydrolyzable halide to yield an epoxy product.

21. The process according to claim 20, wherein said base is selected from the group consisting of sodium hydride, potassium hydride, and lithium hydride.

22. The process according to claim 20, wherein said epoxy product has a hydrolyzable halide content ranging from 0.1 ppm to 100 ppm.

* * * * *

UNITED STATES PATENT AND TRADEMARK OFFICE
CERTIFICATE OF CORRECTION

PATENT NO. : 6,620,907 B2
DATED : September 16, 2003
INVENTOR(S) : Mader, Roger A.

It is certified that error appears in the above-identified patent and that said Letters Patent is hereby corrected as shown below:

Column 5,
Line 13, delete "Theological" and insert in place thereof -- rheological --

Signed and Sealed this

Twentieth Day of July, 2004

JON W. DUDAS
*Acting Director of the United States Patent and Trademark Office*